United States Patent [19]

Lasaitis et al.

[11] Patent Number: 5,102,394
[45] Date of Patent: Apr. 7, 1992

[54] CATHETER ASSEMBLY WITH PROTECTIVE SHIELD

[75] Inventors: Con A. Lasaitis, Waukegan; Sheldon M. Wecker, Libertyville, both of Ill.

[73] Assignee: Abbott Laboratories, Abbott Park, Ill.

[21] Appl. No.: 632,243

[22] Filed: Dec. 19, 1990

[51] Int. Cl.⁵ ............................................. A61M 5/00
[52] U.S. Cl. ....................................... 604/164; 604/263
[58] Field of Search ................ 604/164, 165, 168, 52, 604/53, 54, 190, 198, 158, 159, 160, 263

[56] References Cited

U.S. PATENT DOCUMENTS

| | | | |
|---|---|---|---|
| 4,448,206 | 5/1984 | Martell | 604/190 X |
| 4,828,548 | 5/1989 | Walter | 604/164 |
| 4,850,961 | 7/1989 | Wanderer et al. | 604/53 |
| 4,944,725 | 7/1990 | McDonald | 604/164 |
| 4,944,728 | 7/1990 | Carrell et al. | 604/168 X |

Primary Examiner—John D. Yasko
Attorney, Agent, or Firm—A. Nicholas Trausch

[57] ABSTRACT

A catheter assembly for intravenous therapy includes a protective shield to protect health care personnel from inadvertent injury. The protective shield can be selectively positioned on the assembly to permit manipulation of a needle member of the assembly so that the needle member can be withdrawn from an associated tubular catheter member. After the needle member is withdrawn, it is received within the shield member, and is substantially enclosed therein so that the needle member can disposed of without injury to personnel.

10 Claims, 2 Drawing Sheets

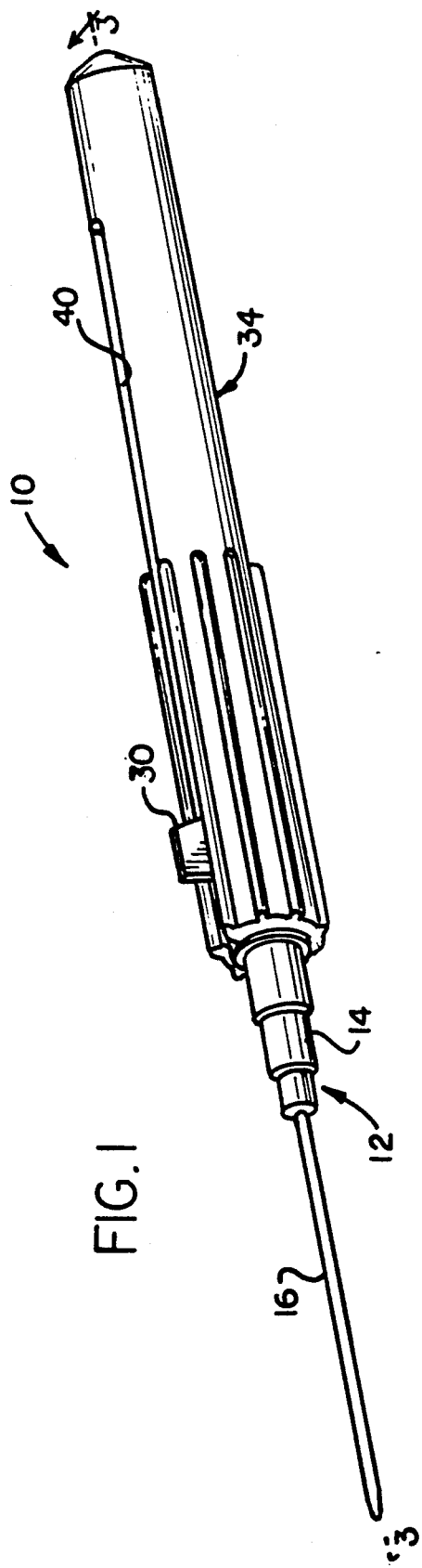
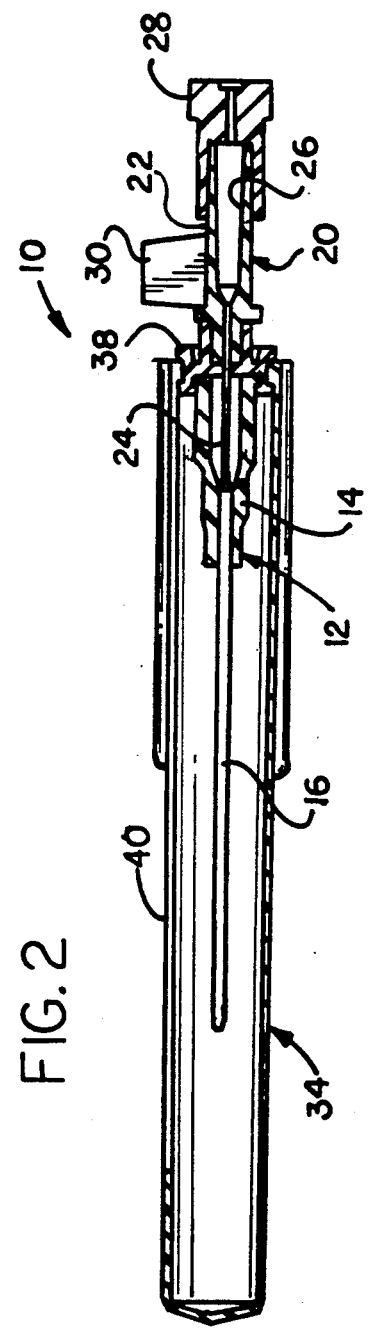
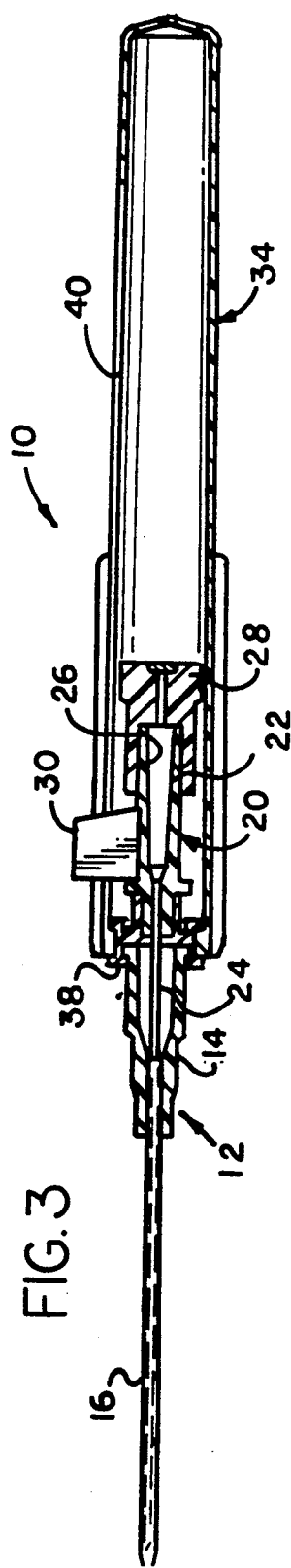

CATHETER ASSEMBLY WITH PROTECTIVE SHIELD

TECHNICAL FIELD

The present invention relates generally to catheter assemblies for intravenous therapy, and more particularly to a catheter assembly including a selectively positionable protective shield which acts to prevent inadvertent injury to health care personnel

BACKGROUND OF THE INVENTION

The use of catheter assemblies is required for a variety of intravenous therapies. A typical catheter assembly includes a generally elongated, tubular portion for insertion into the vein of a patient, and an associated needle member configured for telescopic disposition within the tubular portion of the catheter. The distal or free end of the inner needle member extends just beyond the distal or free end of the tubular portion of the catheter, with the free end of the needle member suitably shaped and sharpened to form the necessary incision for disposition of the tubular portion of the catheter in the vein. After insertion, the inner needle member is then withdrawn from within the catheter, and therapy commenced. The needle member is ordinarily discarded.

In view of the sharpened nature of the needle member, care must be taken in handling to avoid inadvertent injury to health care personnel. While specialized containers (sometimes referred to as sharps containers) are becoming increasingly available for disposal of such needles, a suitable disposal container may not always be at hand at the time of needle removal from the associated catheter. Additionally, the needle is exposed prior to disposal.

The present invention is directed to a catheter assembly configured to protect health care personnel from inadvertent needle injury without the need for a separate, specialized disposal receptacle.

SUMMARY OF THE INVENTION

A catheter assembly embodying the principles of the present invention includes a protective shield which can be selectively removably positioned by health care personnel for intravenous therapy. The shield is configured to permit manipulation of a needle member of the catheter assembly, and to thereafter substantially completely enclose the needle member to reduce the risk of inadvertent injury.

In accordance with the illustrated embodiment, the present catheter assembly includes a catheter member including a base portion, and an elongated tubular portion extending from the base portion. The free or distal end of the tubular portion is positionable in the vein of a patient for therapy.

The assembly further includes a needle member including a hub portion, and an elongated portion extending from the hub portion. The elongated portion of the needle member is positionable in telescopic relationship within the tubular portion of the catheter member, and is preferably configured such that the free end of the inner needle member extends just beyond the free end of the outer, tubular catheter portion.

The catheter assembly further includes a generally elongated, preferably tubular shield member which is selectively, removably positionable on the catheter member. The shield member is positionable in a first position, generally prior to use, wherein the shield member generally encloses the tubular portion of the catheter member. For use of the assembly, the shield member is reversibly movable to a second position on the catheter member, wherein the elongated portion of the needle member can be withdrawn from within the catheter member, with the needle member received within the shield member. Thus, after insertion of the catheter member into the patient, the needle member can be withdrawn into the shield member, which acts to shield a user from inadvertent injury from the needle member.

In the illustrated embodiment, the shield member defines an elongated access slot through which a projection provided on the needle member extends. This arrangement permits manipulation of the needle member from the exterior of the shield member.

In accordance with the illustrated construction, the shield member is removably positionable on the base portion of the catheter member by the provision of an adapter which is removably positionable on the base portion. While the present invention may be embodied without the provision of such an adapter, the adapter can desirably be configured for removal from the catheter member together with the shield member, when it is in its second position, with the needle member enclosed therein. The adapter thus functions in the nature of a closure or cap at the open end of the tubular shield member, thus substantially enclosing and encapsulating the needle member after removal from the associated catheter.

As illustrated, the inner, elongated portion of the needle member is tubular, and communicates with an interior volume defined by the hub portion of the needle member. Attendant to insertion of the assembly into the vein of a patient, capillary and/or venous pressure can result in blood flow through the tubular needle portion and into the hub portion thereof. The hub portion may be formed of transparent material to permit personnel to observe this so-called "flash back".

A venting filter is fitted to the hub portion of the needle member to permit venting of air from within the needle member while preventing flow of liquid through the filter. If desired, the shield member of the assembly can be configured to define an opening near the open end thereof to permit visual inspection of the hub portion of the needle when the shield member is fitted in its second position to the catheter member.

Other features and advantages of the present invention will become readily apparent from the following detailed description, the accompanying drawings, and the appended claims.

BRIEF DESCRIPTION OF THE DRAWINGS

FIG. 1 is a perspective view of a catheter assembly embodying the principles of the present invention;

FIG. 2 is a cross-sectional view of the present catheter assembly showing a protective shield of the assembly in a first position thereof, such as prior to use;

FIG. 3 is a cross-sectional view taken along lines 3—3 of FIG. 1, wherein the protective shield of the assembly is shown in a second position thereof, such as for use;

DETAILED DESCRIPTION

Figure 4:
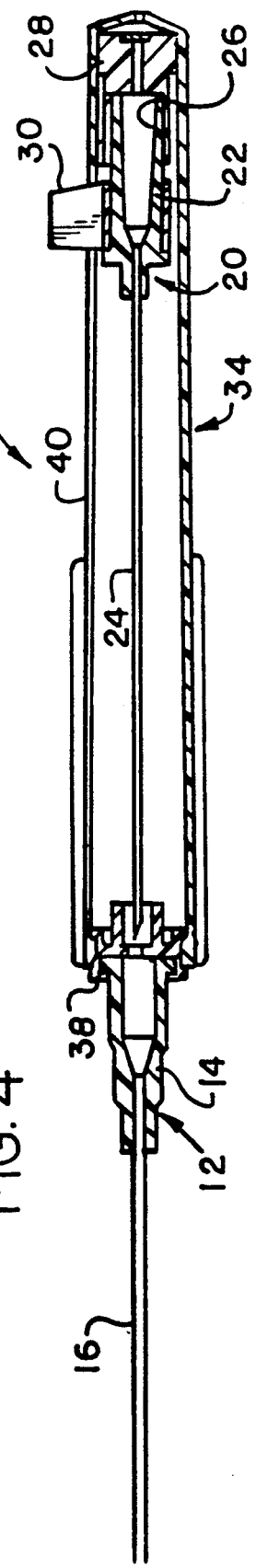
FIG. 4 is a view similar to FIG. 3 illustrating a needle member of the assembly after it has been withdrawn from an associated catheter member of the assembly.

While the present invention is susceptible of embodiment in various forms, there is shown in the drawings and will hereinafter be described a presently preferred embodiment, with the understanding that the present disclosure is to be considered as an exemplification of the invention, and is not intended to limit the invention to the specific embodiment illustrated.

With reference now to the drawings, therein is illustrated a catheter assembly 10 embodying the principles of the present invention. Catheter assembly 10 is configured for intravenous therapy, and includes a catheter member 12 which comprises a base portion 14, and a generally elongated tubular portion 16 extending from the base portion, and communicating with the interior volume defined thereby. The free or distal end of the tubular portion 16 of the catheter member is positionable in the vein of a patient for therapy.

The catheter assembly 10 further includes a needle member 20 which is initially positionable generally within the catheter member 10. Specifically, the needle member includes a hub portion 22, and an elongated tubular portion 24 extending from the hub portion. As illustrated, the free or distal end of the tubular portion 24 of the needle member extends just beyond the free or distal end of the tubular portion 16 of the catheter member when the tubular portion of the needle is telescopically positioned therein. By this arrangement, the free end of the tubular portion of the needle can be suitably configured and sharpened to facilitate insertion of the outer catheter member into the vein of a patient.

Typically, the elongated tubular portion 24 of the needle member communicates with an interior volume 26 defined by the hub portion 22. During catheter insertion, capillary and/or venous pressure can cause blood to flow through the tubular portion 24, and into the interior 26 of the hub portion 22. The hub portion is typically formed from transparent polymeric material so that health care personnel can observe this flow of blood, or "flash back". A venting filter 28 is preferably secured to the hub portion 22 to permit venting of air from within the needle member, while preventing the flow of liquid through the filter.

After insertion of the catheter assembly into a patient, the needle member 22 is withdrawn from within the outer catheter member.

In accordance with the present invention, the needle member 20 includes a tab-like or fin-like projection 30 to facilitate manipulation of the needle member by health care personnel.

The projection 30 is configured for manipulation from the exterior of a protective shield member 34 of the catheter assembly 10. The shield member 34 has a generally elongated, tubular configuration, including an open end which can be selectively removably positioned on catheter member 12 of the assembly. While it is within the purview of the present invention to removably position the shield member 34 directly on the catheter member, the illustrated embodiment includes an adapter 38 removably positionable, preferably by a snap-fit, on the base portion 14 of the catheter member, with the shield member in turn snap-fitted to the adapter. The shield member 34 is positionable in a first position, shown in FIG. 2, so that the shield member generally encloses the tubular portion of the catheter member, such as prior to use of the assembly.

For use of the assembly, the shield member 34 is removed from the catheter member by removal from adapter 38, and is then preferably repositioned on the catheter member by reversibly positioning the shield member in its second position on the adapter, as shown in FIG. 3. In this orientation of the assembly, wherein needle member 20 is positioned so that it extends substantially within the length of catheter member 12, the assembly is ready for use, and insertion into a patient.

To permit manipulation of the needle member 20 when the shield member 34 is in its second position on the catheter member, the shield member defines a generally elongated access slot 40 through which projection 30 extends when the shield member is in its second position. By this configuration, the needle member can be readily manipulated from the exterior of the shield member by movement of projection 30 generally along the length of access slot 40. Manipulation of the needle member in this manner permits the needle member to be withdrawn from within the catheter member, so that the needle member is moved generally from the position shown in FIG. 3 to the position shown in FIG. 4. As will be observed in FIG. 4, it is presently preferred that the shield member be sized relative to the needle member 20 so that the free end of the needle portion 24 does not extend beyond the adapter 38.

After the needle member 20 is withdrawn from within catheter member 12, the needle member, together with the protective shield member 34, is removed from the catheter member 12. Preferably, the adapter 38 is removed together with the shield member 34, thereby substantially enclosing and encapsulating the needle member within the protective shield. Personnel may then safely and conveniently handle and dispose of the needle member as it is contained within the protective shield member 34 and the adapter 38.

Figure 5:
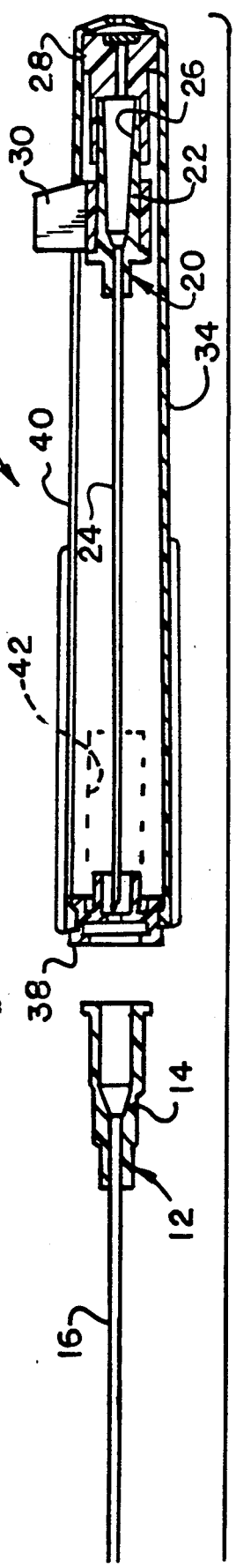
FIG. 5 is a view similar to FIG. 4 illustrating removal of the protective shield with the needle member substantially enclosed therein, after the needle member has been withdrawn from the associated catheter member.

If desired, the shield member 34 may optionally be provided with one or more inspection openings 42 (shown in phantom line in FIG. 5) to permit personnel to visually inspect the hub portion 22 of the needle member for the above-discussed "flash back" when the shield member 34 is in its second position on the catheter member.

From the foregoing, it will be observed that numerous modifications and variations can be effected without departing from the true spirit and scope of the novel concept of the present invention. It is to be understood that no limitation with respect to the specific embodiment is intended or should be inferred. The disclosure is intended to cover by the appended claims all such modifications as fall within the scope of the claims.

What is claimed is:

1. A catheter assembly, comprising:
   a catheter member including a base portion and an elongated tubular portion, extending from said base portion;
   a needle member including a hub portion and an elongated portion extending from said hub portion, said elongated portion of said needle member being positionable in telescopic relationship within the tubular portion of said catheter member; and
   a shield member selectively removably positionable on said catheter member, said shield member being positionable in a first position to generally enclose said tubular portion of said catheter member, and in a second position having a reversed orientation wherein said elongated portion of said needle member can be withdrawn from within said catheter member and said needle member received in said shield member to shield a user from said needle member.

2. A catheter assembly in accordance with claim 1, wherein
said shield member defines access means for manipulating said needle member when said shield member is in said second position on said catheter member, said needle member including means projecting through said access means of said shield member in the second position thereof to permit manipulation of said needle member from the exterior of said shield member.

3. A catheter assembly in accordance with claim 2, wherein
said access means comprises an elongated access slot defined by said shield member, said projecting means extending through said access slot and being movable generally along the length thereof when said shield member is in said second position on said catheter member for withdrawing said needle member from said catheter member.

4. A catheter assembly in accordance with claim 1, including
an adapter removably positionable on the base portion of said catheter member, said shield member being selectively positionable on said catheter member by selective positioning on said adapter, said adapter being removable from said catheter member together with said shield member in the second position thereof with said needle member substantially enclosed within said shield member and said adapter.

5. A catheter assembly in accordance with claim 1, wherein
said elongated portion of said needle member is tubular and communicates with an interior volume defined by said hub portion, said assembly including venting filter means secured to said hub portion for permitting venting of air from within said needle member while preventing flow of liquid through said filter means.

6. A catheter assembly in accordance with claim 5, wherein
said shield member defines means for visually inspecting the hub portion of said needle member when said shield member is in said second position on said catheter member.

7. A catheter assembly comprising:
a catheter member including a base portion and an elongated tubular portion extending from said base portion;
a needle member including a hub portion and an elongated portion extending from said hub portion, said elongated portion of said needle member being positionable in telescopic relationship within the tubular portion of said catheter member, said needle member including a projection extending from the hub portion thereof for manipulating said needle member relative to said catheter member; and
a generally elongated, tubular shield member selectively, removably positionable on said catheter member, said shield member being positionable in a first position to generally enclose said tubular portion of said catheter member, and in a second position having a reversed orientation wherein said elongated portion of said needle member can be withdrawn from within said catheter member and said needle member received in said shield member to shield a user from said needle member, said shield member defining an elongated access slot through which said needle member projection extends when said shield member is in said second position to permit manipulation of said needle member from the exterior of said shield member.

8. A catheter assembly in accordance with claim 7, including:
an adapter removably positionable on the base portion of said catheter member, said shield member being selectively positionable on said catheter member by selective positioning on said adapter, said adapter being removable from said catheter member together with said shield member in the second position thereof with said needle member enclosed within said shield member and said adapter.

9. A catheter assembly in accordance with claim 7, wherein
said elongated portion of said needle member is tubular and communicates with an interior volume defined by said hub portion, said assembly including venting filter means secured to said hub portion for permitting venting of air from within said needle member while preventing flow of liquid through said filter means.

10. A catheter assembly in accordance with claim 9, wherein
said shield member defines means for visually inspecting the hub portion of said needle member when said shield member is in said second position on said catheter member.

* * * * *